(12) United States Patent
Hoffmann-Emery et al.

(10) Patent No.: US 6,531,597 B2
(45) Date of Patent: Mar. 11, 2003

(54) PROCESS FOR PREPARATION OF 2-PHENYL ACETIC ACID DERIVATIVES

(75) Inventors: Fabienne Hoffmann-Emery, Weil am Rhein (DE); Michelangelo Scalone, Birsfelden (CH); Paul Spurr, Riehen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/041,123

(22) Filed: Jan. 8, 2002

(65) Prior Publication Data
US 2002/0156313 A1 Oct. 24, 2002

(30) Foreign Application Priority Data

Feb. 13, 2001 (EP) .............................. 01103284
Nov. 23, 2001 (EP) .............................. 01127405

(51) Int. Cl.[7] ...................... C07D 413/00; C07C 51/12; C07C 57/30
(52) U.S. Cl. ................. 544/124; 562/406; 562/496
(58) Field of Search ................. 562/406, 496; 544/124

(56) References Cited

U.S. PATENT DOCUMENTS 5,536,874 A * 7/1996 Sheldon et al.

FOREIGN PATENT DOCUMENTS

| EP | 1 035 115 | 9/2000 |
|---|---|---|
| WO | WO 00/50398 | 8/2000 |
| WO | WO 00/53572 A1 * | 9/2000 |

OTHER PUBLICATIONS

Lichtenberger et al, No. 112–Sur les Derives du Phenylfluoroforme. I.—Les Trifluoromethyl–benzophenones, 1962, Bulletin Societe Chimique de France, pp. 587–593.*
Solomons, Organic Chemistry, 1992, John Wiley & Sons, Inc., New York, pp. 460–467 and 775–776.*

* cited by examiner

*Primary Examiner*—Johann Richter
*Assistant Examiner*—Paul A. Zucker
(74) *Attorney, Agent, or Firm*—George W Johnston; Patricia S. Rocha-Tramaloni

(57) ABSTRACT

The present invention is a process for the preparation of a compound of formula

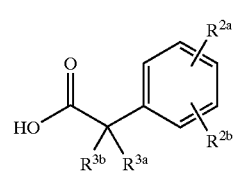

I

The compounds of formula I are valuable intermediates for the manufacture of therapeutically active compounds.

19 Claims, No Drawings

PROCESS FOR PREPARATION OF 2-PHENYL ACETIC ACID DERIVATIVES

FIELD OF INVENTION

The present invention is a process for the preparation of a compound of the formula

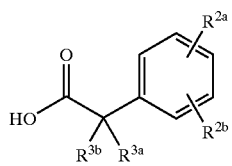

I wherein
$R^{2a}$, $R^{2b}$ are, independently selected from the group consisting of hydrogen, halogen, lower alkoxy, cyano, —COOH, lower alkoxy carbonyl, lower alkyl and lower alkyl substituted by halogen;
$R^{3a}$, $R^{3b}$ are, independently selected from the group consisting of hydrogen, lower alkyl and lower cycloalkyl, or alternatively, $R^{3a}$ and $R^{3b}$ taken together, are —(CH$_2$)$_n$— wherein n=2, 3 or 5.

BRIEF SUMMARY OF THE INVENTION

The compounds of formula I are valuable intermediate products for the preparation of therapeutically active compounds of formula

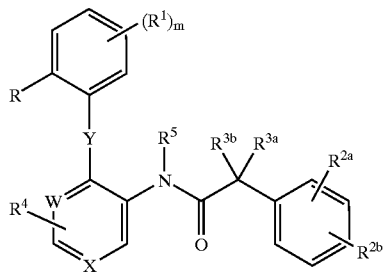

II wherein
R is hydrogen; lower alkyl; lower alkoxy; halogen; or trifluoromethyl;
$(R^1)_m$ are, independently from each other, hydrogen or halogen; or
R and $R^1$ may be together —CH═CH—CH═CH—;
$R^{2a}$, $R^{2b}$, $R^{3a}$, $R^{3b}$ have the meanings mentioned above;
$R^4$ is hydrogen; halogen; lower alkyl; lower alkoxy; —N(R$^5$)$_2$; —N(R$^5$)S(O)$_2$— lower alkyl; —N(R$^5$)C(O) R$^5$ or a cyclic tertiary amine of the group

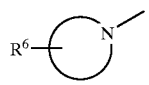

$R^5$ is, independently from each other, hydrogen; $C_{3-6}$-cycloalkyl; benzyl; or lower alkyl;
$R^6$ is hydrogen; hydroxy; lower alkyl; —N(R$^5$)CO— lower alkyl; hydroxy-lower alkyl; cyano; —CHO; or a 5- or 6 membered heterocyclic group, optionally bonded via an alkylene group;

Y is a single bond; —(CH$_2$)$_n$—; —O—; —S—; —SO$_2$—; —C(O)—; or —N(R$^5$)—;
X is ═N—; —CH═; or —C(Cl)═;
W is —CH═; or ═N—;
m is 0,1,2,3 or 4.

Examples of compounds of formula II can be found among the 4-phenyl-pyridine derivatives such as 2-(3,5-bis-trifluoromethyl-phenyl)-N-methyl-N-(6-morpholin-4-yl-4-o-tolyl-pyridin-3-yl)-isobutyramide and among the 4-phenyl pyrimidin derivatives such as 2-(3,5-bis-trifluoromethyl-phenyl)-N-methyl-N-(2-morpholin-4-yl-4-o-tolyloxy-pyrimidin-5-yl)-isobutyramide. It has been surprisingly found that the compounds of formula II are antagonists of the neurokinin-1 (NK-1, substance P) receptor. Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

Compounds of formula II are described e.g. in EP-A-1035115 and WO 00/50398.

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like. Preferred lower alkyl groups are groups with 1 to 4 carbon atoms. A preferred "lower alkyl substituted by halogen" is trifluoromethyl.

The term "lower alkoxy" denotes a group wherein the alkyl residues are as defined above, and which is attached via an oxygen atom.

The term "halogen" denotes chlorine, iodine, fluorine and bromine.

The term "cycloalkyl" denotes a saturated carbocyclic group, containing 3–7 carbon atoms.

The term "cyclic tertiary amine" denotes, for example, pyrrol-1-yl, imidazol-1-yl, piperidin-1-yl, piperazin-1-yl, morpholin-4-yl, thiomorpholin-4-yl, 1-oxo-thiomorpholin-4-yl or 1,1-dioxo-thiomorpholin-4-yl.

The term "5 or 6 membered heterocyclic group" denotes, for example pyridinyl, pyrimidinyl, oxadiazolyl, triazolyl, tetrazolyl, thiazolyl, thienyl, furyl, pyranyl, pyrrolyl, imidazolyl, pyrazolyl, isothiazolyl, piperazinyl or piperidyl.

The term "aryl" denotes 5 or 6 membered carbocyclic aromatic compounds or condensed carbocyclic aromatic compounds such as phenyl and naphthyl.

The compounds of formula II can be manufactured according to e.g. WO 00/50398, i.e. by converting a compound of formula

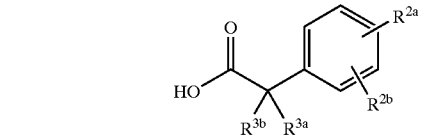

I into the corresponding chloro or bromo acid halide, and by reacting the obtained halide with a compound of formula

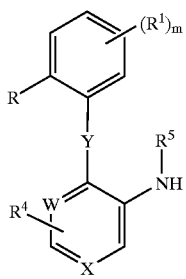

III to a compound of formula II, wherein the definition of the substituents is given above.

Compounds of general formula I can be manufactured, on their turn, by successively alkylating (twice) a compound of formula

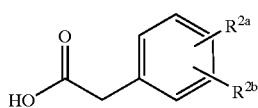

IV with an $R^{3a}$-halide (in the presence of a strong base such as BuLi) to a compound of general formula

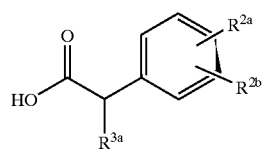

V and I, respectively.

This method for manufacturing the compounds of general formula I is high-yielding but requires the use of the expensive starting materials of formula IV. Furthermore, the dialkylated product of general formula I may contain rather high quantities of the mono alkylated intermediate V and/or of over alkylated compounds, e.g. at the benzene ring. These by-products are quite difficult to remove by crystallization and their concentration in the final product mixture strongly varies in accordance with the reaction conditions. Consequently the above process is unsuitable for scale-up.

Alternatively, the acid of formula IV can be converted into the corresponding ester of formula

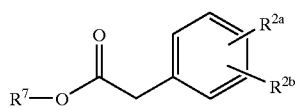

VI wherein $R^{2a}$, $R^{2b}$, $R^{3a}$, $R^{3b}$ have the significance given above and $R^7$ is lower alkyl. The ester of formula VI is then dialkylated and subsequently saponified (or hydrolyzed) to the compound of formula I.

The second variant of the state-of-the-art method allows to overcome the above purification problem, but it involves an additional esterification/saponification (hydrolysis) step, thus still increasing the costs and complexity of the whole manufacturing process.

The problem at the root of the present invention is therefore to provide a process for preparing the compounds of formula I which can overcome the disadvantages mentioned above.

This problem is solved, according to the invention, by a process for preparing the compounds of formula I comprising the steps of:

reacting a Grignard derivative of a compound of formula

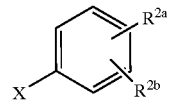

VII wherein X is Cl, Br or I, with a compound of formula

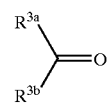

VIII to a compound of formula

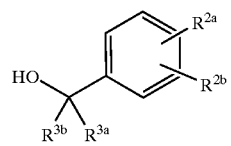

IX carbonylating the compound of formula IX in the presence of a strong acid, wherein the compound of formula I is obtained.

The process according to the present invention allows to obtain yields which are higher than those provided by the above described conventional process, no major side-products are observed and no complex purification operations are necessary.

Furthermore, the reactants used (formulae VII and VIII) are much cheaper than those applied in the above conventional processes (compounds of formula IV) and are easily available on the market, so that the overall manufacturing costs of compounds of formula I, and therefore also of compounds of formula II, are strongly decreased.

The process according to the present invention is therefore suitable for the scale-up production of the compounds of formula II.

According to a preferred embodiment of the present invention $R^{2a}$, $R^{2b}$ are, independently selected from the group consisting of hydrogen, halogen, lower alkyl and lower alkyl substituted by halogen, lower alkoxy, or cyano, and $R^{3a}$, $R^{3b}$ are independently selected from the group consisting of hydrogen, lower alkyl, lower cycloalkyl or, alternatively, $R^{3a}$ and $R^{3b}$ taken together form —$(CH_2)_n$— with n=2,3 or 5.

According to another preferred embodiment of the present invention, $R^{2a}$ and $R^{2b}$ are independently selected from the group consisting of lower alkoxy; lower alkoxy carbonyl; lower alkyl and lower alkyl substituted by halogen; and $R^{3a}$ and $R^{3b}$ are independently lower alkyl or, alternatively, $R^{3a}$ and $R^{3b}$ taken together form —$(CH_2)_5$—.

According to a still more preferred embodiment of the invention, the process is applied for the manufacture of 2-(3,5-bis-trifluoromethyphenyl)-2-methyl-propionic acid.

The Grignard reaction (step a) takes place in an ether, such as diethyl ether, tetrahydrofuran, dipropyl ether, dibutyl ether and the like, or in a mixture of ethers and aromatic solvents such as toluene and xylene. The reaction is carried out at atmospheric pressure and at a temperature varying between about 15° C. and the boiling point of the reaction mixture itself (reflux). The purity of the alcohol intermediate of formula IX is not critical; it can be as low as 70%, for preparing the acid of formula I in a purity of at least 97%.

The carbonylation reaction (step b) is preferably performed at a temperature varying between about −20° C. and about 60° C., more preferably between about 10° C. and about 30° C., and in the presence of a chlorinated solvent such as dichloromethane, dichloroethane, chloroform, carbon tetrachloride and dichlorobenzene.

The addition of a strong acid is necessary for the carbonylation reaction to proceed. Preferred acids are the fluorinated sulfonic acids of formula $C_nF_{2n+1}SO_3H$ (n=0–20, preferably 0–6), $C_2F_5O$—$C_2F_4SO_3H$ and mixtures thereof. The acids $FSO_3H$, $CF_3SO_3H$ and mixtures thereof are particularly preferred. The strong acid is preferably added in amounts varying between about 1 and about 10 molar equivalents, preferably between about 2 and about 5 molar equivalents.

According to a preferred embodiment of the present invention water is added to the reactants mixture of step b) in an amount up to about 5 molar equivalents (relative to the alcohol of formula IX), preferably in an amount varying between about 0.1 and about 1 molar equivalents and, still more preferably, in an amount varying between about 0.2 and about 0.7 molar equivalents. The addition of water is not mandatory but it generally enables a reproducible increase of the selectivity towards the compound of formula I. The addition of a reagent such as formic acid, which under the reaction conditions decomposes to give water and CO, has the same effect.

The carbonylation may take place at pressures of CO varying between about 1 and about 500 bar, preferably between about 10 and about 100 bar and, even more preferably, between about 20 and about 60 bar.

The concentration, defined as gram of alcohol of formula IX per gram of solvent used, may vary between about 1 and about 30%, preferably between about 1 and about 15%, without implying major consequences on yield and selectivity towards the compounds of formula I.

In order to avoid possible decomposition of the alcohol IX during the charging of the reactor, i.e. before the carbonylation starts, it may be appropriate, on a large scale, to add it to the mixture of solvent, acid and water (if necessary), already under CO pressure. The carbonylation reaction is then almost instantaneous. Accordingly, the carbonylation step may take place either in a semi-batch or in a continuous flow reactor.

Another aspect of the present invention concerns a process for the manufacture of compounds of formula II comprising the subsequent steps of converting a compound of formula I into the corresponding chloro or bromo acid halide and reacting the halide with a compound of formula III to a compound of formula II, wherein the compound of formula I is obtained by the steps of:
    reacting a Grignard derivative of a compound of formula VII with a compound of formula VIII, to a compound of formula IX; and
    carbonylating the compound of formula IX wherein the compound of formula I is obtained.

Preferably, the process according to the present invention is applied for preparing therapeutically active compounds 2-(3,5-bis-trifluoromethyl-phenyl)-N-methyl-N-(6-morpholin-4-yl-4-o-tolyl-pyridin-3-yl)-isobutyramide or 2-(3,5-bis-trifluoromethyl-phenyl)-N-methyl-N-(2-morpholin-4-yl-4-o-tolyloxy-pyrimidin-5-yl)-isobutyramide.

By way of examples, preferred embodiments of the present invention will now be described. Unless stated to the contrary, all of the examples listed below were actually prepared and characterized.

EXAMPLE 1

Synthesis of 2-(3,5-bis-Trifluoromethyl-phenyl)-propan-2-ol 16.10 g (0.659 mol) of magnesium turnings was treated under argon in 450 ml of diethyl ether with 150 g (0.507 mol) of 3,5-bis-trifluoromethylbromobenzene at 33° C. for 1.5 h. Then a solution of 56.0 ml (0.763 mol) of acetone in 100 ml of diethylether was added at 16–22° C. under stirring. 110 ml of 25% Ammonium chloride solution was added at ca. 20° C. after 1.5 h to the reaction mixture and the suspension stirred for 1 h. The organic phase was dried over sodium sulfate, rotary evaporated and finally dried at 35° C. and 10 mbar, affording 136.96 g of 2-(3,5-bis-trifluoromethyl-phenyl)-propan-2-ol, which had a 99.2% purity according to GC analysis. Light yellow crystals, m.p. 59–60° C.

EXAMPLE 2

Synthesis of 2-(3,5-bis-Trifluoromethylphenyl)-2-methyl-propionic Acid with Addition of Water A 185 ml stainless steel autoclave was charged under argon with 25 ml of dichloromethane, 22.30 ml (0.25 mol) of trifluoromethane sulfonic acid and 0.45 ml (25 mmol) of water. The autoclave was sealed and pressurized with 30 bar of carbon monoxide. Then under stirring a solution of 14.13 g (50 mmol) of 2-(3,5-bis-trifluoromethyl-phenyl)-propan-2-ol in 35 ml of dichloromethane was added with a pump within 50 min at 20° C. and the reaction mixture was stirred for additional 2 h. Thereafter the autoclave was vented and the biphasic reaction mixture was treated in an ice bath with a solution of 13.2 g of sodium hydroxide in 130 ml of water. The organic phase was removed and the aqueous phase was washed with dichloromethane. After filtration, 35 ml of 36.5% hydrochloric acid solution were added to the aqueous phase under stirring at 8–12° C. The resulting suspension was extracted twice with dicloromethane and, after drying with sodium sulfate, the organic phase was evaporated and the solid residue dried at room temperature and 10 mbar vacuum. 14.98 g of 2-(3,5-bis-trifluoromethylphenyl)-2-methyl-propionic acid were isolated as light brown crystals with m.p. 105.5–107° C. and 99.0% purity according to HPLC analysis.

EXAMPLE 3

Synthesis of 2-(3,5-bis-Trifluoromethylphenyl)-2-methyl-propionic Acid without Addition of Water A 2 l stainless steel autoclave was charged under argon with 250 ml of dichloromethane and 218.5 ml (2.45 mol) of trifluoromethane sulfonic acid. The autoclave was sealed and pressurized with 30 bar of carbon monoxide. Then under stirring a solution of 136.7 g (0.49 mol) of 2-(3,5-bis-trifluoromethyl-phenyl)-propan-2-ol in 350 ml of dichloromethane was added with a pump within 50 min at 20° C. and the reaction mixture was stirred for additional 2 h. An isolation procedure analogous to that described in Example 2 afforded, after acidification of the aqueous phase with hydrochloric acid, a precipitate which was isolated by filtration and dried at 55° C. and 10 mbar to constant weight.

138.31 g of 2-(3,5-bis-trifluoromethylphenyl)-2-methyl-propionic acid were isolated as light yellow crystals with m.p. 106–106.5° C. and 98% purity according to HPLC analysis.

EXAMPLES 4.1–4.6

The examples in Table 1 were run in analogy to example 2 (water added) or example 3 (no water added).

TABLE 1

| Example No. | Total CH$_2$Cl$_2$ (ml) | SM[a] (g) | Sulfonic acid[b] (ml) | H$_2$O (ml) | % yield (isolated) | % content (HPLC) |
|---|---|---|---|---|---|---|
| 4.1 | 37 | 2.7 | 4.5 | 0.1 | 96 | 98 |
| 4.2[e] | 37 | 2.7 | 2.7 | 0.1 | 53 | n.d. |
| 4.3 | 60 | 14.1 | 22.3 | None | 94 | 97 |
| 4.4 | 650 | 50 | 79.2 | None | 96 | 97 |
| 4.5[c] | 32 | 2.7 | 1.4[d] | None | 69 | 97 |
| 4.6[c] | 32 | 2.7 | 2.3[d] | None | 86 | 98 |

[a]Starting material (SM): 2-(3,5-bis-trifluoromethyl-phenyl)-propan-2-ol
[b]Sulfonic acid is in all examples CF$_3$SO$_3$H, with exception of 4.5, where it is FSO$_3$H.
[c]P = 50 bar of CO.
[d]Molar ratio sulfonic acid/SM is 2.5.
[e]Molar ratio sulfonic acid/SM is 3.0. The reaction was heated for additional 3 h. % Yield was determined by GC. N.d. means not determined.

EXAMPLES 5.1–5.3

The examples in Table 2 were run in analogy to example 3 (no water added) using starting material of various purity.

TABLE 2[a]

| Example No. | Total CH$_2$Cl$_2$ (ml) | SM (g) | Purity of SM (GC) | CF$_3$SO$_3$H (ml) | % yield (isolated) | % content (HPLC) |
|---|---|---|---|---|---|---|
| 5.1 | 56 | 10.7 | 77 | 17.6 | 87 | 96 |
| 5.2 | 35 | 8.0 | 86 | 13.0 | 85 | 96 |

[a]Starting Material (SM): 2-(3,5-bis-trifluoromethyl-phenyl)-propan-2-ol

EXAMPLE 6

Synthesis of 2-(3,5-bis-Trifluoromethyl-phenyl)-2-methyl-propionyl Chloride 15.0 g (50 mmol) 2-(3,5-bis-trifluoromethyl-phenyl)-2-methyl-propionic acid were dissolved in 127.5 ml dichloromethane in the presence of 0.75 ml DMF. 8.76 ml (2 eq.) Oxalyl chloride were added and after 4.5 hours, the solution was rotary evaporated to dryness. 9 ml Toluene were added and the resulting solution was again rotary evaporated, then dried under high vacuum yielding 16.25 g (quant.) of 2-(3,5-bis-trifluoromethyl-phenyl)-2-methyl-propionyl chloride as a yellow oil of 86% purity according to HPLC analysis.

NMR (250 MHz, CDCl$_3$): 7.86 (br s, 1H); 7.77, (br s, 2H, 3 H$_{arom}$); 1.77 (s, 6H, 2 CH$_3$).

Synthesis of 2-(3,5-bis-Trifluoromethyl-phenyl)-N-[4[(2-chloro-phenyl)-6-morpholin-4-yl-pyridin-3-yl]-N-methyl-isobutyramide 8.56 g (28.1 mmol) [4-(2-Chloro-phenyl)-6-morpholin-4-yl-pyridin-3-yl]-methyl-amine were dissolved in 50 ml dichloromethane in the presence of 5.5 ml (1.4 eq.) triethylamine and cooled to 0° C. A solution of 10.8 g (1.05 eq.) 2-(3,5-bistrifluoromethyl-phenyl)-2-methyl-propionyl chloride (step a) in 10 ml dichloromethane was added slowly and after 2 hours, 80 ml water was added. After 15 minutes stirring, the phases were separated, the aqueous phase was extracted with 2 portions of 80 ml dichloromethane and the combined organic extracts were washed with 80 ml water, 80 ml 2% aqueous NaOH, 80 ml water and 80 ml 5% aqueous NaHCO$_3$, dried over Na$_2$SO$_4$ and concentrated under reduced pressure. Crystallization from 40 ml 2-propanol and 20 ml ethanol at −20° C. yielded 14.2 g (86%) of 2-(3,5-bis-trifluoromethyl-phenyl)-N-[4-(2-chloro-phenyl)-6-morpholin-4-yl-pyridin-3-yl]-N-methyl-isobutyramide as a white powder of m.p.=134.4–135.5° C.

EXAMPLE 7.1–7.4

Examples 7.1–7.4 (Table 3) were run in analogy to Example 2 (water added) using different starting materials.

The carbonylation substrates were prepared by reaction of the aryl Grignard reagent with the corresponding ketone in diethyl ether as solvent. The alcohol of experiment 7.4 was prepared according to P. Knochel et al, Angew. Chem. Int. Ed. 1998, 37, 1701.

TABLE 3

| Example No. | Substrate, conditions | | Product | % yield (isolated) | % content (GC) | Analyses |
|---|---|---|---|---|---|---|
| 7.1 | 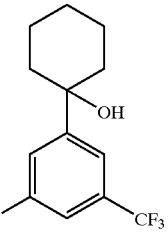 | 2.65 g, 8.49 mmol CH2Cl2 35 ml CF3CO2H 3.8 ml H2O 0.076 ml CO 51 bar | 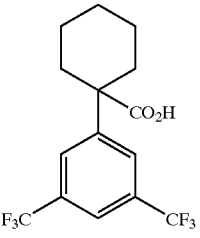 (2.23 g) | 78 | 89 | m.p. 108° C. (after recryst. from hexane, 98% pure) MS (M$^+$): 340.1 |

TABLE 3-continued

| Example No. | Substrate, conditions | Product | % yield (isolated) | % content (GC) | Analyses |
|---|---|---|---|---|---|
| 7.2 | 1.50 g, 0.010 mmol CH2Cl2 35 ml CF3CO2H 4.5 ml H2O 0.090 ml CO 30 bar | (0.34 g) | 19 | 93 | m.p. 90° C. (after recryst. from hexane/MeOH, 99% pure) MS (M − H): 177.0 |
| 7.3 | 1.67 g, 10.0 mmol CH2Cl2 35 ml CF3CO2H 4.5 ml H2O 0.09 ml CO 30 bar | (0.69 g) | 36 | 80 | m.p. 115° C. (after recryst. from t-butyl methylether) MS (M − H): 193.1 |
| 7.4 | 0.77 g, 3.70 mmol CH2Cl2 35 ml CF3CO2H 1.7 ml H2O 0.33 ml CO 30 bar | * (0.42 g) | 55 | 95 | m.p. 200° (after sublimation, 98% pure) MS (M+): 208.2 |

*The product of the carbonylation of 4-(1-hydroxy-1-methyl-ethyl)-benzoic acid ethyl ester was 4-(1-carboxy-1-methyl-ethyl)-benzoic acid ethyl ester. However, the corresponding benzoic acid is obtained: a) at least in part already during the carbonylation reaction by acid-catalyzed reaction with excess water and b) during the work-up of the reaction mixture by saponification, when this was extracted with aqueous sodium hydroxide.

We claim:

1. A process for the preparation of a compound of formula

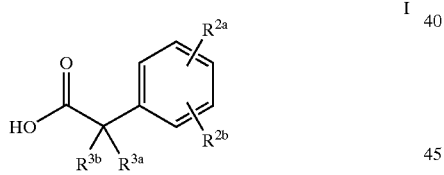

I wherein $R^{2a}$, $R^{2b}$ are each independently selected from the group consisting of hydrogen, halogen, lower alkoxy, cyano, —COOH, lower alkoxy carbonyl, lower alkyl and lower alkyl substituted by halogen;

$R^{3a}$, $R^{3b}$ are each independently selected from the group consisting of hydrogen, lower alkyl and lower cycloalkyl, or alternatively, $R^{3a}$ and $R^{3b}$ together are, —(CH$_2$)$_n$— wherein n=2,3 or 5;

comprising a) reacting a Grignard derivative of a compound of formula

VII wherein X is Cl, Br or I, with a compound of formula

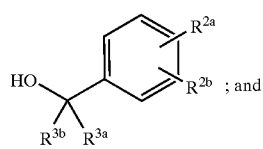

VIII forming a compound of formula

IX

; and b) carbonylating the compound of formula IX by reacting compound IX in a carbonylation mixture in the presence of a reagent consisting essentially of a sufficient quantity of a strong acid thereby forming the compound of formula I.

2. The process of claim 1, wherein $R^{2a}$, $R^{2b}$ are each independently selected from the group consisting of hydrogen, halogen, lower alkoxy, cyano, lower alkyl and lower alkyl substituted by halogen.

3. The process of claim 1, wherein

R$^{2a}$, R$^{2b}$ are each independently selected from the group consisting of lower alkoxy, lower alkoxy carbonyl, lower alkyl, and lower alkyl substituted by halogen; and R$^{3a}$, R$^{3b}$ are each independently selected from lower alkyl or alternatively, R$^{3a}$ and R$^{3b}$ taken together form the group —(CH$_2$)$_5$—.

4. The process of claim 3, wherein R$^{2a}$ and R$^{2b}$ are lower alkyl substituted by halogen.

5. The process of claim 4 wherein said lower alkyl substituted by halogen is tri-fluoromethyl thereby forming 2-(3,5-bis-trifluoromethyphenyl)-2-methyl-propionic acid.

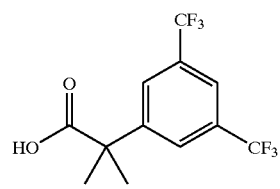

6. The process of claim 1, wherein step a) is carried out at atmospheric pressure and at a temperature varying between about 15° C. and the boiling point of the reaction mixture.

7. The process of claim 1, wherein step b) is carried out at a temperature varying between about −20° C. and about 60° C. and at a CO pressure varying between about 1 and about 500 bar.

8. The process of claim 7, wherein step b) is carried out at a temperature varying between about 10° C. and about 30° C.

9. The process of claim 8, wherein step b) is carried out at a CO pressure varying between about 10 and about 100 bar.

10. The process of claim 9, wherein step b) is carried out at a CO pressure varying between about 20 and about 60 bar.

11. The process of claim 1, wherein the strong acid is selected from the group consisting of C$_n$F$_{2n+1}$SO$_3$H, wherein n is between 0 and 20, C$_2$F$_5$O—C$_2$F$_4$SO$_3$H and mixtures thereof.

12. The process of claim 11 wherein n is between 0 and 6.

13. The process of claim 11, wherein the strong acid is selected from the group consisting of FSO$_3$H, CF$_3$SO$_3$H and mixtures thereof.

14. The process of claim 1, further comprising adding water to the reactants mixture of step b) in an amount up to about 5 molar equivalents relative to the compound of formula IX.

15. The process of claim 14, wherein the water is added in an amount between about 0.1 and about 1 molar equivalents.

16. The process claim 15, wherein the water is added in an amount between about 0.2 and about 0.7 molar equivalents.

17. A process for the preparation of a compound of formula II

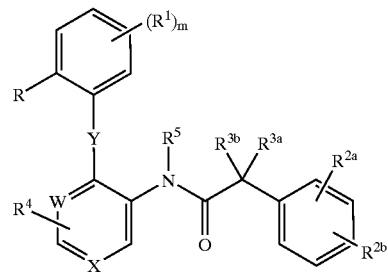

wherein

R is selected from the group consisting of hydrogen, lower alkyl; lower alkoxy, halogen, and trifluoromethyl;

(R$^1$)$_m$ are independently selected from the group consisting of hydrogen; or halogen, or alternatively, R and R$^1$ taken together form —CH═CH—CH═CH—;

R$^{2a}$, R$^{2b}$, R$^{3a}$, R$^{3b}$ have the meaning given in claim 1;

R$^4$ is selected from the group consisting of hydrogen, halogen, lower alkyl lower alkoxy, —N(R$^5$)$_2$, —N(R$^5$)S(O)$_2$-lower alkyl, —N(R$^5$)C(O)R$^5$, and a cyclic tertiary amine of the group

R$^5$ is independently selected from the group consisting of hydrogen; C$_{3-6}$-cycloalkyl; benzyl, and lower alkyl;

R$^6$ is selected from the group consisting of hydrogen, hydroxy, lower alkyl, —N(R$^5$)CO-lower alkyl, hydroxy-lower alkyl, cyano, —CHO; and a 5- or 6 membered heterocyclic group, or alternatively, a 5- or 6-membered heterocyclic group bonded via an alkylene group, Y is a single bond; —(CH$_2$)$_n$—; —O—; —S—; —SO$_2$—; —C(O)—; or —N(R$^5$)—;

X is ═N—; —CH═; or —C(Cl)═;

W is —CH═; or ═N—; and m is 1,2,3 or 4, comprising converting a compound of formula

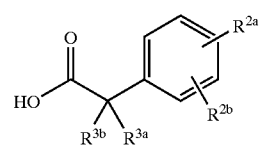

into the corresponding acid chloro or bromo halide, and reacting the obtained halide with a compound of formula forming a compound of formula II, wherein the compound of formula I is formed by the steps comprising a) reacting a Grignard derivative of a compound of formula

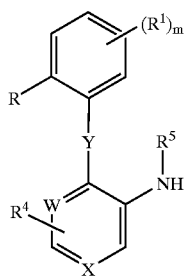

III

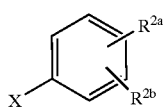

VII wherein X is Cl, Br or I, with a compound of formula

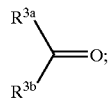

VIII forming a compound of formula

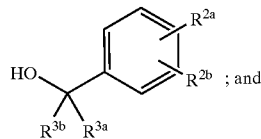

IX b) carbonylating the compound of formula IX in a carbonylation mixture in the presence of a reagent consisting essentially of a sufficient quantity of a strong acid, thereby forming the compound of formula I.

18. The process of claim 17, wherein $R^{2a}$ and $R^{2b}$ are each independently selected from the group consisting of hydrogen, halogen, lower alkoxy, cyano, lower alkyl and lower alkyl substituted by halogen; and $R^{3a}$ and $R^{3b}$ are each independently selected from the group consisting of hydrogen, lower alkyl and lower cycloalkyl, or alternatively, $R^{3a}$ and $R^{3b}$ together are —$(CH_2)_n$— wherein n=2,3 or 5.

19. The process of claim 17, wherein $R^{2a}$ and $R^{2b}$ are lower alkyl substituted by halogen and $R^4$ is a cyclic tertiary amine of the group

thereby forming compounds of formula II 2-(3,5-bis-trifluoromethyl-phenyl)-N-methyl-N-(6-morpholin-4-yl-4-o-tolyl-pyridin-3-yl)-isobutyramide and 2-(3,5-bis-trifluoromethyl-phenyl)-N-methyl-N-(2-morpholin-4-yl-4-o-tolyloxy-pyrimidin-5-yl)-isobutyramide.

* * * * *